United States Patent
Wang et al.

(10) Patent No.: US 9,320,801 B2
(45) Date of Patent: Apr. 26, 2016

(54) CYCLOSPORINE-CONTAINING NON-IRRITATIVE NANOEMULSION OPHTHALMIC COMPOSITION

(71) Applicants: INDUSTRY-ACADEMIC COOPERATION FOUNDATION, YONSEI UNIVERSITY, Seoul (KR); Huons Co., Ltd., Gyeonggi-do (KR)

(72) Inventors: Sung Joon Wang, Seoul (KR); Kwang Ho Cha, Incheon (KR); Han Kang, Incheon (KR); Bo Kyung Sun, Incheon (KR)

(73) Assignee: HUONS CO., LTD (KR)

( * ) Notice: Subject to any disclaimer, the term of this patent is extended or adjusted under 35 U.S.C. 154(b) by 0 days.

(21) Appl. No.: 14/398,012

(22) PCT Filed: Jan. 22, 2013

(86) PCT No.: PCT/KR2013/000509
§ 371 (c)(1),
(2) Date: Oct. 30, 2014

(87) PCT Pub. No.: WO2013/165074
PCT Pub. Date: Nov. 7, 2013

(65) Prior Publication Data
US 2015/0125494 A1    May 7, 2015

(30) Foreign Application Priority Data

Apr. 30, 2012    (KR) .......................... 10-2012-0045708

(51) Int. Cl.
| | | |
|---|---|---|
| *A61K 38/13* | (2006.01) | |
| *A61K 47/44* | (2006.01) | |
| *A61K 9/107* | (2006.01) | |
| *A61K 9/00* | (2006.01) | |
| *A61K 47/10* | (2006.01) | |
| *A61K 47/32* | (2006.01) | |
| *A61K 47/26* | (2006.01) | |
| *A61K 47/36* | (2006.01) | |

(52) U.S. Cl.
CPC ............... *A61K 47/44* (2013.01); *A61K 9/0048* (2013.01); *A61K 9/1075* (2013.01); *A61K 38/13* (2013.01); *A61K 47/10* (2013.01); *A61K 47/32* (2013.01); *A61K 47/26* (2013.01); *A61K 47/36* (2013.01)

(58) Field of Classification Search
CPC ... A61K 38/13; A61K 9/0048; A61K 9/1075; A61K 47/32; A61K 47/36; A61K 47/26; A61K 47/10; A61K 47/44
See application file for complete search history.

(56) References Cited

U.S. PATENT DOCUMENTS

| | | | |
|---|---|---|---|
| 5,951,971 A | 9/1999 | Kawashima et al. | |
| 6,057,289 A | 5/2000 | Mulye | |
| 2005/0196370 A1* | 9/2005 | Yu ........................ | A61K 9/0048 424/70.13 |

FOREIGN PATENT DOCUMENTS

| | | | | |
|---|---|---|---|---|
| CN | 101244256 A | * | 8/2008 | ............. A61K 38/13 |
| JP | 05-058906 | | 3/1993 | |
| JP | H0558906 A | | 3/1993 | |
| JP | 2011-105754 | | 6/2011 | |
| KR | 10-0669510 | | 1/2007 | |
| KR | 10-2010-0135857 | | 10/2010 | |
| KR | 10-1008189 | | 1/2011 | |
| WO | 94/25068 | | 11/1994 | |
| WO | 2009/091894 | | 7/2009 | |

OTHER PUBLICATIONS

Machine translation of KR 101008189 B1, pp. 1-15, accessed Sep. 29, 2015.*
Machine translation of CN 101244256 A, pp. 1-37, accessed Sep. 29, 2015.*

* cited by examiner

*Primary Examiner* — Julie Ha
*Assistant Examiner* — Li Ni Komatsu
(74) *Attorney, Agent, or Firm* — Riverside Law LLP

(57) ABSTRACT

Provided is an ophthalmic composition containing cyclosporine as an active ingredient and including polyethoxylated castor oil or polyethoxylated hydrogenated castor oil, and a method of preparing the same. Particularly, the ophthalmic composition is prepared as a nanoemulsion having a particle diameter of 100 nm or less simply by mixing and stirring an oil phase and an aqueous phase without using a high speed stirring or shearing machine, so that it is very physiochemically stable and storable for a long time. In addition, the ophthalmic composition causes no irritation to eyes.

10 Claims, 4 Drawing Sheets

CYCLOSPORINE-CONTAINING NON-IRRITATIVE NANOEMULSION OPHTHALMIC COMPOSITION

CROSS REFERENCE TO RELATED APPLICATIONS

This application is the U.S. national phase application filed under 35 U.S.C. §371claiming benefit to International Patent Application No. PCT/KR2013/000509, filed on Jan. 22, 2013, which is entitled to priority under 35 U.S.C. §119(a)-(d) to Korea application no. 10-2012-0045708, filed Apr. 30, 2012, each of which application is hereby incorporated herein by reference in its entirety.

TECHNICAL FIELD

The present invention relates to an ophthalmic emulsion containing cyclosporine, and more particularly, to a stable ophthalmic composition which causes no irritation when applied to eyes and has an emulsion particle size of 100 nm or less, and a method of preparing the same.

BACKGROUND ART

An ophthalmic preparation containing an immunosuppressant may contain cyclosporine, sirolimus, tacrolimus, or a derivative thereof. Among these, cyclosporine, which is known to be effective in treatment of dry eye syndrome, includes cyclosporine A, cyclosporine B, cyclosporine C and cyclosporine D, but cyclosporine A and derivatives thereof are the most widely researched.

However, it is generally known that since cyclosporine has a very low water solubility of approximately 20 to 30 μg/ml, it is difficult to prepare a drug compound containing cyclosporine that is dissolved in an aqueous medium, and such a drug compound is the commercially available Restasis® (cyclosporine ophthalmic emulsion 0.05%).

An emulsion refers to a liquid-liquid dispersion system in which at least one liquid is dispersed in another liquid with which it is immiscible, and the emulsion generally has a size distribution ranging from 0.1 to several tens of micrometers. Microemulsions are thermodynamically unstable, and eventually separate through various routes, for example, flocculation, sedimentation, creaming, Ostwald ripening, coalescence, etc. In this connection, when sizes of dispersion-phase emulsion particles are reduced to a nano scale, according to the Brown's movement between the particles, in a kinetic aspect, stability of an emulsion can be significantly enhanced, and the commercially available Restasis® is a nanoemulsion prepared by reducing a particle size of a dispersed phase to a nano scale.

Meanwhile, in processes of preparing known nanoemulsions including Restasis®, a high pressure homogenizer that applies high physical power to an emulsion, or a high speed stirring or shearing machine such as a microfluidizer is used. The preparation method requires large preparation equipment, consumes high costs, and applies high energy to an emulsion, so that a temperature is highly increased during emulsification, and it is difficult to apply to a component vulnerable to heat. In addition, Restasis® prepared by the above-described method has non-uniform particle size in the emulsion, and thus more flocculation occurs and creaming rapidly progresses, which results in a problem of long-term storage. In addition, when the high pressure homogenizer is used, due to instability of phospholipids at a high temperature (e.g., oil separation, creaming, etc.), smell change or high temperature stability is reduced, and particularly, since a distribution of particles of a dispersed phase is relatively wider, it is difficult to ensure uniform product quality in every preparation lot.

In relation to the above-described problem, the inventors developed a technique of preparing a nanoemulsion ophthalmic composition having an average particle size of 200 nm or less only by simple mixing and stirring oil and an aqueous component in the preparation of the emulsion (Korean Patent No. 1008189). However, when the patent composition is actually applied to eyes, the eyes become very irritated.

DISCLOSURE

Technical Problem

The present invention is directed to providing a nanoemulsion ophthalmic composition containing cyclosporine which is prepared simply by mixing cyclosporine with a solubilizer, and has a particle diameter of 100 nm or less and long lasting physiochemical stability, and causes no irritation when applied to eyes.

However, the technical problems to be solved in the present invention are not limited to the above descriptions, and other problems that are not described will be clearly understood by one of ordinary skill in the art from the following descriptions.

Technical Solution

One aspect of the present invention provides a nanoemulsion ophthalmic composition including cyclosporine at 0.01 to 1 wt %; polyethoxylated castor oil or polyethoxylated hydrogenated castor oil at 0.5 to 9.79 wt %; and a phosphate buffer at 90 to 99.29 wt %, and since the composition uses the polyethoxylated castor oil or polyethoxylated hydrogenated castor oil as a solubilizer of the cyclosporine, a separate oil or an emulsifier is unnecessary in the nanoemulsion ophthalmic composition, and the composition can be prepared by simple mixing.

In one exemplary embodiment of the present invention, the nanoemulsion has an average particle size of 100 nm or less, and preferably 50 nm or less.

In another exemplary embodiment of the present invention, the cyclosporine is cyclosporine A.

The ophthalmic composition of the present invention may further include a thickening agent. The thickening agent used in the present invention may be, but is not limited to, at least one selected from the group consisting of hyaluronic acid or a salt thereof, chitosan, hydroxypropylmethylcellulose, hydroxypropylcellulose, hydroxyethylcellulose, polyvinyl pyrrolidone, carboxymethylcellulose, carbomer, glycerin, and polyethyleneoxide. Preferably, the thickening agent is hyaluronic acid or a salt thereof. The thickening agent may be included at 0.1 to 5 wt % with respect to a total weight of the ophthalmic composition of the present invention.

In still another exemplary embodiment of the present invention, the ophthalmic composition of the present invention may further include ethanol as a sub-solvent. The ethanol may be included at 0.1 to 3 wt % with respect to a total weight of the ophthalmic composition.

Yet another aspect of the present invention provides a method of preparing a non-irritative nanoemulsion ophthalmic composition containing cyclosporine, which includes the following operations: producing a first solution by dissolving cyclosporine A in a solubilizer; producing a second solution by dissolving a thickening agent in phosphate buffer; and mixing the first solution with the second solution, and simply stirring the resulting mixture without using a high speed stirring or shearing machine.

As the solubilizer, polyethoxylated castor oil or polyethoxylated hydrogenated castor oil may be used, and ethanol may be further included in the solubilizer. In addition, as the thickening agent, glycerin and/or sodium hyaluronate may be used.

Advantageous Effects

The present invention can advantageously provide a cyclosporine-containing nanoemulsion ophthalmic composition which causes no irritation to eyes. In addition, the ophthalmic composition of the present invention can be prepared as a nanoemulsion having a smaller particle diameter in the emulsion than the conventional ophthalmic emulsion and showing even distribution simply by mixing cyclosporine with a solubilizer without using a high pressure homogenizer, and has increased physiochemical stability, thereby being storable for a long time. In addition, since the emulsion has a small particle diameter of 100 nm or less and even distribution, there is no blurred vision or irritation to eyes when eye drops are applied.

MODE FOR INVENTION

Figure 1:
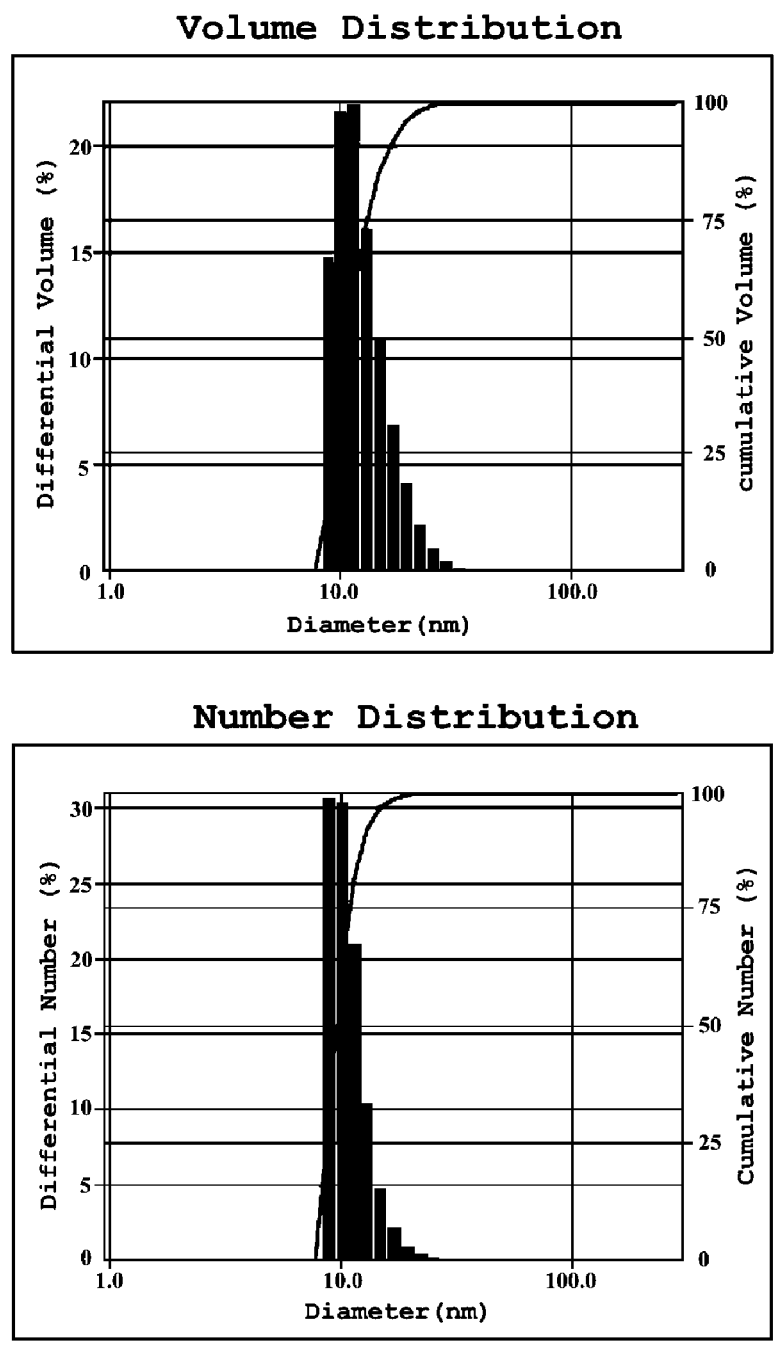
FIG. 1 is a result obtained by measuring a particle size of a nanoemulsion prepared according to an exemplary embodiment of the present invention.

The inventors completed the present invention as a result of developing a nanoemulsion prepared simply by mixing and stirring cyclosporine and a solubilizer that has a particle diameter of 100 nm or less and long-lasting physiochemical stability, and causes no irritation.

The cyclosporine-containing nanoemulsion ophthalmic composition of the present invention is a nanoemulsion ophthalmic composition including cyclosporine at 0.01 to 1 wt %; polyethoxylated castor oil or polyethoxylated hydrogenated castor oil at 0.5 to 9.79 wt %; and a phosphate buffer at 90 to 99.29 wt %, and the composition uses the polyethoxylated castor oil or polyethoxylated hydrogenated castor oil as a solubilizer for the cyclosporine, and thus does not need to separately use oil and an emulsifier, and is prepared simply by mixing.

As an active ingredient of the cyclosporine of the present invention, cyclosporine A, a cyclosporine A derivative, cyclosporine B, cyclosporine C, or cyclosporine D may be included. Preferably, the present invention includes cyclosporine A.

As a solubilizer for the cyclosporine, the active ingredient of the ophthalmic composition of the present invention, polyethoxylated castor oil or polyethoxylated hydrogenated castor oil may be used.

Castor oil or hydrogenated castor oil has excellent cyclosporine solubility, and the commercially available Restasis® ophthalmic composition also uses castor oil as a solubilizer. However, castor oil or hydrogenated castor oil is a triglyceride prepared by binding recinoleic acid or stearic acid with glycerol, and to disperse castor oil or hydrogenated castor oil in water, an emulsifier is needed. In addition, for stability of the oil phase dispersed in water, particles of the emulsion should be ground in units of several hundreds of nanometers through a high pressure homogenizer.

In this regard, in the present invention, unlike the conventional nanoemulsion ophthalmic composition, since polyethoxylated castor oil or polyethoxylated hydrogenated castor oil in which a hydrophilic group, that is, ethylene oxide, is directly modified to a fatty acid of castor oil or hydrogenated castor oil is used as the solubilizer of cyclosporine instead of castor oil or hydrogenated castor oil, a cyclosporine-containing ophthalmic nanoemulsion composition in which the solubility of cyclosporine is maintained and cyclosporine is easily dispersed in an aqueous solution can be provided. That is, using polyethoxylated castor oil or polyethoxylated hydrogenated castor oil, unlike the conventional art, addition of a separate oil and emulsifier is not needed, and a nanoemulsion composition having an average particle size of 100 nm or less can be prepared, thereby providing an ophthalmic composition causing no irritation or blurred vision when actually applied to eyes.

In one exemplary embodiment of the present invention, the ophthalmic composition of the present invention may further include ethanol as a sub-solvent of the cyclosporine.

In another exemplary embodiment of the present invention, the ophthalmic composition of the present invention may further include a thickening agent. The thickening agent may be included at 0.5 to 5 wt % with respect to the entire ophthalmic composition. The thickening agent used in the present invention is not limited, and thickening agents for medicines or foods generally used in the art may be used. For example, the thickening agent may be at least one selected from the group consisting of hyaluronic acid or a salt thereof, glycerin, chitosan, hydroxypropylmethylcellulose (HPMC), hydroxypropylcellulose (HPC), hydroxyethylcellulose (HEC), polyvinyl pyrrolidone (PVP), carboxymethylcellulose (CMC), a carbomer (carbomer), and polyethyleneoxide (PEO).

In addition, the present invention provides a method of preparing a cyclosporine-containing nanoemulsion ophthalmic composition, and the method may include the following operations:

producing a first solution by dissolving cyclosporine A in a solubilizer;

producing a second solution by dissolving a thickening agent in a phosphate buffer; and mixing and simply stirring the first solution and the second solution.

As the solubilizer, polyethoxylated castor oil or polyethoxylated hydrogenated castor oil may be used, and ethanol may be further included in the solubilizer.

The method of the present invention, when needed, may further include adding a pH controller and/or an isotonizing agent to control pH and osmotic pressure of eye drops.

Hereinafter, to help understanding of the present invention, Examples will be provided. However, the following Examples are merely provided so that the present invention can be more easily understood, and the scope of the present invention is not limited to the following Examples.

EXAMPLES

Example 1

Preparation of Nanoemulsion According to Kind of Solubilizer

Cyclosporine was mixed into respective solubilizers according to component ratios of 1-A to 1-J of Table 1 (first solution). Glycerin and poloxamer 188 were mixed into a phosphate buffer having pH of 7.2 according to each composition, and the first solution was dispersed in the resulting solution, thereby preparing an emulsion. As an isotonizing agent, NaCl was used, and osmolarity was adjusted to 300 mOsmol.

TABLE 1

Emulsion composition containing various solubilizers

| composition | Component | | | | | | | | | |
|---|---|---|---|---|---|---|---|---|---|---|
| | 1-A | 1-B | 1-C | 1-D | 1-E | 1-F | 1-G | 1-H | 1-I | 1-J |
| Cyclosporine A | 0.05% | 0.05% | 0.05% | 0.05% | 0.05% | 0.05% | 0.05% | 0.05% | 0.05% | 0.05% |
| Polyethyoxylated castor oil | 5% | — | — | — | — | — | — | — | — | — |
| Polyethoxylated hydrogenated castor oil | — | 5% | — | — | — | — | — | — | — | — |
| Castor oil | — | — | 5% | — | — | — | 5% | — | — | — |
| Cottonseed oil | — | — | — | 5% | — | — | — | 5% | — | — |
| Soybean oil | — | — | — | — | 5% | — | — | — | 5% | — |
| Olive oil | — | — | — | — | — | 5% | — | — | — | 5% |
| Poloxamer 188 | — | — | — | — | — | — | 3.3% | 3.3% | 3.3% | 3.3% |
| Glycerin | 2.2% | 2.2% | 2.2% | 2.2% | 2.2% | 2.2% | 2.2% | 2.2% | 2.2% | 2.2% |
| Phosphate buffer | suitable amount | suitable amount | suitable amount | suitable amount | suitable amount | suitable amount | suitable amount | suitable amount | suitable amount | suitable amount |
| Isotonizing agent | suitable amount | suitable amount | suitable amount | suitable amount | suitable amount | suitable amount | suitable amount | suitable amount | suitable amount | suitable amount |

Example 2

Preparation of Emulsion Composition According to Change in Component Ratio of Solubilizer/Ethanol Compositions 2-A to 2-I were prepared by the same method as that for preparing the composition 1-A in Example 1 by controlling amounts of polyethyoxylated castor oil and ethanol as shown in Table 2.

TABLE 2

Emulsion composition according to change in component ratio of solubilizer/Ethanol

| composition | Component | | | | | | | | |
|---|---|---|---|---|---|---|---|---|---|
| | 2-A | 2-B | 2-C | 2-D | 2-E | 2-F | 2-G | 2-H | 2-I |
| Cyclosporine A | 0.05% | 0.05% | 0.05% | 0.05% | 0.05% | 0.05% | 0.05% | 0.05% | 0.05% |
| Polyethyoxylated castor oil | 5% | 4% | 3% | 5% | 4% | 3% | 5% | 4% | 3% |
| Ethanol | 1% | 1% | 1% | 0.5% | 0.5% | 0.5% | — | — | — |
| Sodium hyaluronate | 0.1% | 0.1% | 0.1% | 0.1% | 0.1% | 0.1% | 0.1% | 0.1% | 0.1% |
| Glycerin | 2.2% | 2.2% | 2.2% | 2.2% | 2.2% | 2.2% | 2.2% | 2.2% | 2.2% |
| Phosphate buffer | suitable amount | suitable amount | suitable amount | suitable amount | suitable amount | suitable amount | suitable amount | suitable amount | suitable amount |
| Isotonizing agent | suitable amount | suitable amount | suitable amount | suitable amount | suitable amount | suitable amount | suitable amount | suitable amount | suitable amount |

Example 3

Preparation of Emulsion Composition Containing Various Thickening Agents

Compositions 3-A to 3-F were prepared by the same method as that for preparing the composition 1-A in Example 1 by controlling the kind and amount of a thickening agent as shown in Table 3.

TABLE 3

Emulsion composition containing various thickening agents

| composition | 3-A | 3-B | 3-C | 3-D | 3-E | 3-F |
|---|---|---|---|---|---|---|
| Cyclosporine A | 0.05% | 0.05% | 0.05% | 0.05% | 0.05% | 0.05% |
| Polyethyoxylated castor oil | 5% | 5% | 5% | 5% | 5% | 5% |
| Ethanol | 1% | 1% | 1% | 1% | 1% | 1% |
| Sodium hyaluronate | 0.1% | 0.5% | — | — | — | — |
| Carbomer | — | — | 0.1% | 0.5% | — | — |
| Chitosan | — | — | — | — | 0.1% | 0.5% |
| Glycerin | 2.2% | 2.2% | 2.2% | 2.2% | 2.2% | 2.2% |
| Phosphate buffer | suitable amount | suitable amount | suitable amount | suitable amount | suitable amount | suitable amount |
| Isotonizing agent | suitable amount | suitable amount | suitable amount | suitable amount | suitable amount | suitable amount |

Example 4

Preparation of Emulsion Composition According to Concentration of Cyclosporine A Compositions 4-A to 4-E were prepared by changing a concentration of cyclosporine A as shown in Table 4.

TABLE 4

Emulsion composition according to concentration of cyclosporine A

| Component | 4-A | 4-B | 4-C | 4-D | 4-E |
|---|---|---|---|---|---|
| Cyclosporine A | 0.01% | 0.03% | 0.05% | 0.1% | 0.2% |
| Polyethyoxylated castor oil | 5% | 5% | 5% | 5% | 5% |
| Ethanol | 1% | 1% | 1% | 1% | 1% |
| Sodium hyaluronate | 0.1% | 0.1% | 0.1% | 0.1% | 0.1% |
| Glycerin | 2.2% | 2.2% | 2.2% | 2.2% | 2.2% |
| Phosphate buffer | suitable amount | suitable amount | suitable amount | suitable amount | suitable amount |
| Isotonizing agent | suitable amount | suitable amount | suitable amount | suitable amount | suitable amount |

Experimental Example 1

Measurement of Particle Diameter Size of Emulsion

Average particle diameter sizes were measured with respect to the emulsions prepared in Examples 1 to 4 using a laser scattering particle size analyzer, and the results are shown in Table 6. Here, the commercially available Restasis® 0.05% eye drops produced by Samil Allergan (Lot No.: 69297) were used as a control (control composition) 1, and a 6-G preparation disclosed as an example in Korean Patent No. 1008189 was used as a control 2.

TABLE 5

Components and contents of composition of control 2

| Component | 6-G |
|---|---|
| Cyclosporine A | 0.05% |
| Oleoyl macrogoglyceride | 2.5% |
| Poloxamer 188 | 3.3% |
| Glycerin | 1.6% |
| Chitosan | 0% |
| NaOH | suitable amount |
| Distilled water | suitable amount |

As shown in Table 6, as the emulsion preparation prepared in Example 1, the compositions 1-A to 1-B using polyethoxylated castor oil or polyethoxylated hydrogenated castor oil as a solubilizer could provide a nanoemulsion having a particle diameter of 100 nm or less without using a separate emulsifier.

In comparison, the compositions 1-C to 1-F did not form an emulsion without using an emulsifier, and the compositions 1-G to 1-J used an emulsifier, thereby having a very large average particle diameter of several micrometers.

Meanwhile, it can be seen that all the compositions 2-A to 4-E according to the present invention could prepare nanoemulsions having a particle diameter of 100 nm or less, and had a smaller particle diameter than the control 1 prepared using a high pressure homogenizer.

Figure 2:
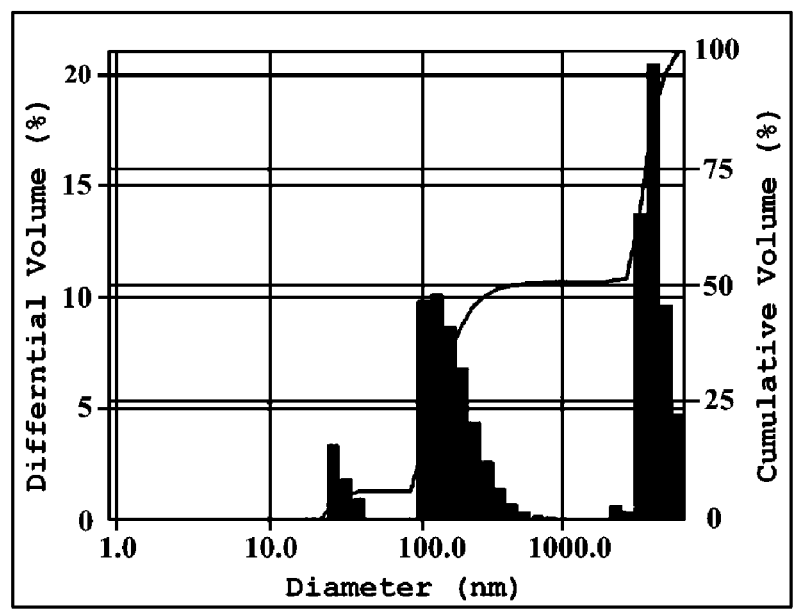
FIG. 2 is a result obtained by measuring a particle size of the commercially available Restasis®.
Figure 2:
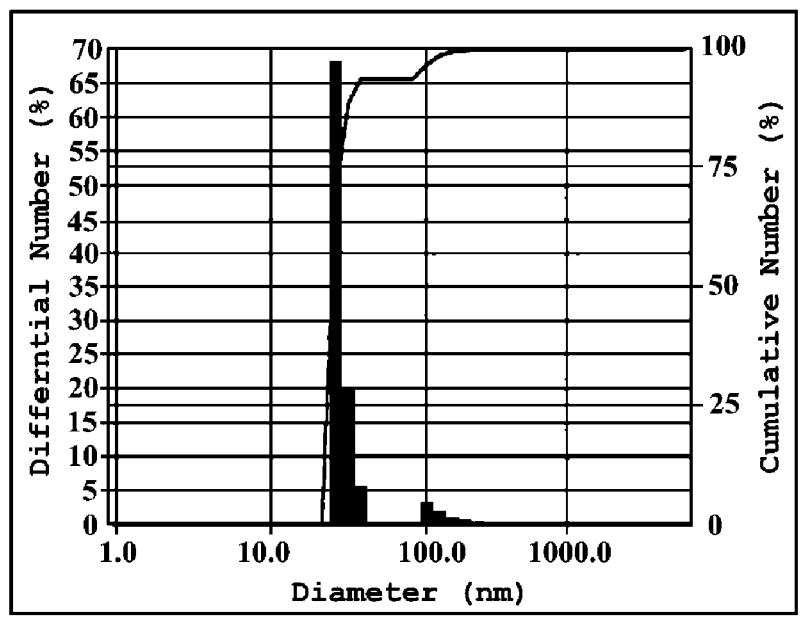

In addition, as shown in FIG. 1, it can be seen that the composition 2-C of the present invention had a small particle size of 17.4 nm and even single particle distribution, but as shown in FIG. 2, the control 1 had an average particle size of 328.4 nm and increased particle distribution since small particles were agglomerated.

Generally, based on Stokes' law with respect to stability of the emulsion, as the particle size of the emulsion could be reduced, probability of precipitation could be reduced.

From this result, as the composition of the present invention includes cyclosporine as fine particles in a dosage form of a lipid dissolved in water, and is uniformly prepared, the composition is expected to be able to be used as eye drops causing no irritation.

TABLE 6

Comparison of particle size between emulsions according
to the present invention and control compositions

| Composition | Particle size (nm) |
|---|---|
| 1-A | 17.5 ± 1.4 |
| 1-B | 18.3 ± 2.4 |
| 1-C | — |
| 1-D | — |
| 1-E | — |
| 1-F | — |
| 1-G | 4219 ± 54 |
| 1-H | 6529 ± 43 |
| 1-I | 1759 ± 86 |
| 1-J | 4391 ± 131 |
| 2-A | 16.9 ± 1.1 |
| 2-B | 17.5 ± 1.9 |
| 2-C | 17.4 ± 3.1 |
| 2-D | 17.5 ± 2.2 |
| 2-E | 17.7 ± 0.7 |
| 2-F | 17.3 ± 2.9 |
| 2-G | 17.2 ± 3.3 |
| 2-H | 17.7 ± 1.1 |
| 2-I | 17.3 ± 2.7 |
| 3-A | 16.9 ± 1.1 |
| 3-B | 24.5 ± 4.4 |
| 3-C | 19.2 ± 2.9 |
| 3-D | 33.7 ± 3.9 |
| 3-E | 18.4 ± 3.3 |
| 3-F | 41.4 ± 5.9 |
| 4-A | 17.2 ± 2.5 |
| 4-B | 17.7 ± 1.9 |
| 4-C | 16.9 ± 1.1 |
| 4-D | 16.7 ± 2.9 |
| 4-E | 17.5 ± 3.3 |
| control 1 | 328.4 ± 12 |
| control 2 | 92.6 ± 11.3 |

Experimental Example 2

Stability Test for Emulsions of the Present Invention

Changes in particle size and pH of the compositions 1-A, 1-B, 3-A, 3-C, and 3-E of the present invention according to time were tested at room temperature, and the results are shown in Tables 7 and 8. As shown in Tables 7 and 8, it can be seen that the compositions of the present invention did not have significant changes in particle size and emulsion pH according to time.

The results mean that the compositions of the present invention could be stored for a long time since they were physiochemically stable.

TABLE 7

Change in particle size (nm) of emulsions according to time

| | Day | | | |
|---|---|---|---|---|
| Composition | 0 day | 7 day | 15 day | 30 day |
| Composition 1-A | 17.5 ± 1.4 | 18.2 ± 2.1 | 17.9 ± 1.5 | 19.1 ± 0.5 |
| Composition 1-B | 18.3 ± 2.4 | 17.4 ± 2.2 | 17.5 ± 1.7 | 19.2 ± 1.5 |
| Composition 3-A | 16.9 ± 1.1 | 18.5 ± 0.9 | 19.7 ± 2.4 | 17.4 ± 2.9 |
| Composition 3-C | 19.2 ± 2.9 | 22.1 ± 3.4 | 21.7 ± 1.7 | 20.9 ± 1.9 |
| Composition 3-E | 18.4 ± 3.3 | 21.6 ± 4.5 | 22.8 ± 1.9 | 21.7 ± 3.3 |

TABLE 8

Change in pH of emulsions according to time

| | Day | | | |
|---|---|---|---|---|
| Composition | 0 day | 7 day | 15 day | 30 day |
| Composition 1-A | 7.22 ± 0.12 | 7.25 ± 0.08 | 7.19 ± 0.22 | 7.22 ± 0.17 |
| Composition 1-B | 7.25 ± 0.17 | 7.29 ± 0.15 | 7.30 ± 0.17 | 7.31 ± 0.11 |
| Composition 3-A | 7.29 ± 0.18 | 7.32 ± 0.11 | 7.27 ± 0.23 | 7.28 ± 0.09 |
| Composition 3-C | 7.21 ± 0.24 | 7.25 ± 0.16 | 7.22 ± 0.19 | 7.27 ± 0.05 |
| Composition 3-E | 7.26 ± 0.09 | 7.22 ± 0.10 | 7.22 ± 0.25 | 7.28 ± 0.10 |

Experimental Example 3

Evaluation of Transparency of Eye Drops

Through a transparency test for eye drops, transparency of the ophthalmic compositions 4-C to 4-E prepared according to the present invention and the control 1 (Restasis®) were evaluated to observe transparency and blurred vision when the eye drops were applied to eyes beforehand in vitro.

Particularly, using a saline solution (0.9% NaCl) instead of tears, 2 ml each of the ophthalmic compositions was taken, and the saline was added thereto to evaluate transparency with the naked eye. The results are shown in Table 9.

TABLE 9

| | Transparency test | | | |
|---|---|---|---|---|
| | Composition 4-C | Composition 4-D | Composition 4-E | Control 1 |
| Original state | transparent | transparent | transparent | opaque |
| Up to 50 ml of saline solution | transparent | transparent | transparent | opaque |
| 50 ml of saline solution | transparent | transparent | transparent | slightly milky semi-transparent |
| 50 ml or more of saline solution | transparent | transparent | transparent | semi-transparent to transparent |

As shown in Table 9, in case of the conventional commercially available product, Restasis®, to become transparent from opaque when applied to eyes, a saline solution having an amount of approximately 25 times the eye drops (50 ml for 2 ml of the eye drops) was needed. That is, when 0.4 ml of the conventional product is applied to eyes, vision can be expected to become clear after the eye drops are diluted by a flow of 10 ml of tears.

However, it can be seen that the ophthalmic compositions 4-C to 4-E according to the present invention were transparent from the beginning, and maintained their transparency, so that they did not cause undesirable actions such as blurred vision.

Experimental Example 4

Irritation Test for Eye Drops

An irritation test, that is, a 3x3 crossover test, was performed on three subject groups of four as shown in Table 10. The test was performed for a total of three periods. After the composition 2-C, control 1, and control 2 according to the present invention were applied to the subjects, a degree of irritation was scored, which is shown in Table 11.

Figure 3:
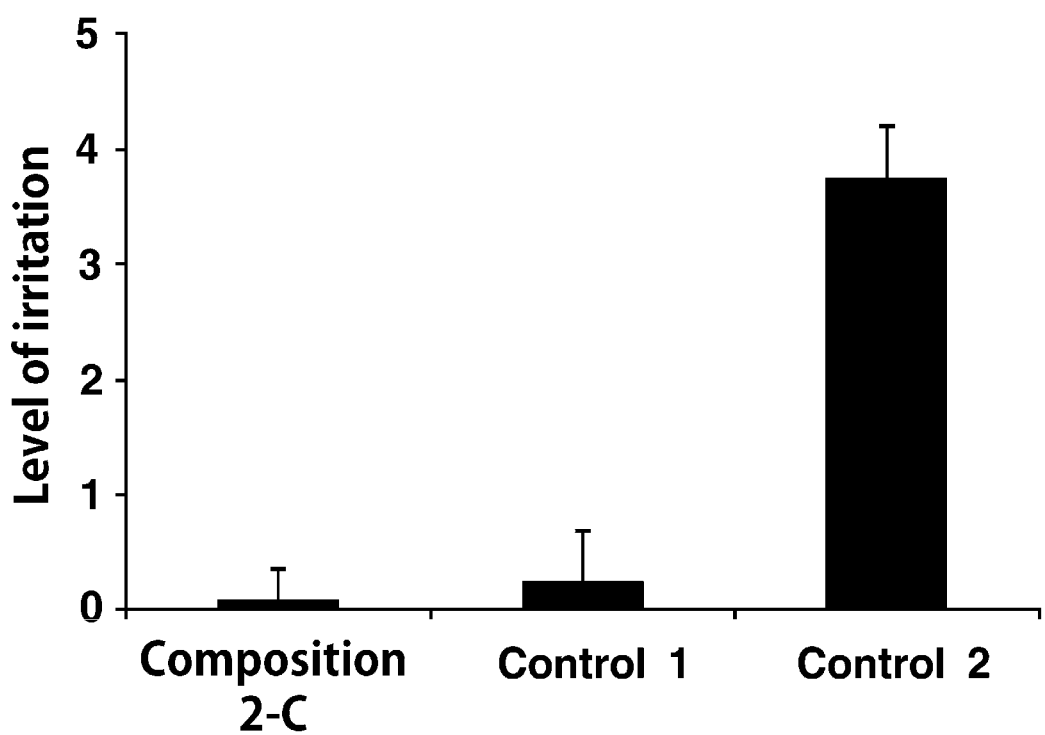
FIG. 3 is a result of an irritation test performed for an ophthalmic composition according to an exemplary embodiment of the present invention and control eye drops (control).

As shown in Table 11 and FIG. 3, the composition 2-C prepared according to the present invention had excellent effects with almost no irritation, control 2 caused very severe irritation, and the control 1 caused slight to mild irritation.

TABLE 10

3 × 3 Latin square crossover test models

| Subject No. | Period I | Period II | Period III |
|---|---|---|---|
| A1 | Composition 2-C | control 1 | control 2 |
| A2 | | | |
| A3 | | | |
| A4 | | | |
| B1 | control 2 | Composition 2-C | control 1 |
| B2 | | | |
| B3 | | | |
| B4 | | | |
| C1 | control 1 | control 2 | Composition 2-C |
| C2 | | | |
| C3 | | | |
| C4 | | | |

TABLE 11

Results of irritation test

| | Composition 2-C | control 1 | control 2 |
|---|---|---|---|
| A1 | 0 | 0 | 3 |
| A2 | 0 | 0 | 4 |
| A3 | 0 | 0 | 4 |
| A4 | 0 | 0 | 4 |
| B1 | 0 | 0 | 3 |
| B2 | 0 | 1 | 4 |
| B3 | 0 | 0 | 3 |
| B4 | 1 | 0 | 4 |

TABLE 11-continued

Results of irritation test

| | Composition 2-C | control 1 | control 2 |
|---|---|---|---|
| C1 | 0 | 0 | 4 |
| C2 | 0 | 1 | 4 |
| C3 | 0 | 0 | 4 |
| C4 | 0 | 1 | 4 |

0; no irritation,
+1; slight irritation,
+2~+3; mild irritation,
+4; severe irritation Experimental Example 5

Schirmer's Tear Test

To evaluate efficacy of the ophthalmic composition according to the present invention, the following test was performed on albino rabbits.

Specifically, the rabbits were divided into 2 groups of six, and 50 μl of a 0.1% atropine sulfate solution was applied three times a day (at 9 a.m., 2 p.m., and 7 p.m.) (when the 0.1% atropine sulfate solution was applied to eyes of the rabbit, a temporal dry eye syndrome can be caused). After 5 minutes, the right eyes of each group were treated with a saline solution, and the left eyes thereof were treated with the composition 2-C according to the present invention or Restasis® (refer to Table 12).

TABLE 12

Method for Schirmer's tear test

| | 1 group | 2 group |
|---|---|---|
| Right eye | 1% Atropine sulfate + Normal saline (0.9%) | 1% Atropine sulfate + Normal saline (0.9%) |
| Left eye | 1% Atropine sulfate + Composition 2-C eye drops of the present invention | 1% Atropine sulfate + Restasis ® |

The Schirmer's tear test was performed for 5 days by measuring an amount of tears using a test paper of the Schirmer's tear test at 9 p.m. after 2, 3, 4 and 5 days of the test. The results are shown in Table 13.

TABLE 13

Results of Schirmer's tear test (amount of tear (mm))

Composition 2-C

| | Rabbit 1 | | Rabbit 2 | | Rabbit 3 | | Rabbit 4 | | Rabbit 5 | | Rabbit 6 | |
|---|---|---|---|---|---|---|---|---|---|---|---|---|
| Day | Right eye | Left eye | Right eye | Left eye | Right eye | Left eye | Right eye | Left eye | Right eye | Left eye | Right eye | Left eye |
| 0 | 15 | 10 | 17 | 21 | 13 | 9 | 10 | 8.5 | 10 | 12 | 14.5 | 11.5 |
| 2 | 6.5 | 15 | 10 | 12.5 | 7 | 7.5 | 5 | 7.5 | 9 | 13.5 | 5 | 9.5 |
| 3 | 11 | 13.5 | 6.8 | 12 | 6 | 6.5 | 5 | 6.5 | 10 | 9.5 | 5 | 8.5 |
| 4 | 9.5 | 10 | 11 | 18.5 | 5 | 10.2 | 7 | 7.5 | 6.8 | 10.5 | 9 | 18 |
| 5 | 11 | 16 | 7 | 18 | 5 | 7 | 5 | 7 | 5 | 10.5 | 7 | 11 |

TABLE 13-continued

Results of Schirmer's tear test (amount of tear (mm))

Control 1

Rabbit

| | Rabbit 7 | | Rabbit 8 | | Rabbit 9 | | Rabbit 10 | | Rabbit 11 | | Rabbit 12 | |
|---|---|---|---|---|---|---|---|---|---|---|---|---|
| Day | Right eye | Left eye | Right eye | Left eye | Right eye | Left eye | Right eye | Left eye | Right eye | Left eye | Right eye | Left eye |
| 0 | 12 | 9.5 | 10.5 | 14 | 8.5 | 9.5 | 10 | 13 | 9.5 | 9.5 | 10 | 12 |
| 2 | 5 | 7.5 | 5.5 | 11 | 11 | 12 | 5.8 | 6.2 | 7.5 | 6 | 12.5 | 12 |
| 3 | 5 | 6.8 | 10.3 | 9.2 | 10 | 14.5 | 5 | 6.2 | 5 | 5 | 9.5 | 14.5 |
| 4 | 6.5 | 6 | 9.5 | 10 | 12 | 11 | 5.5 | 7.2 | 8 | 11.5 | 10 | 12 |
| 5 | 6 | 8 | 10 | 8 | 14 | 22 | 5 | 5 | 7.5 | 9.5 | 10.5 | 15 |

Figure 4:
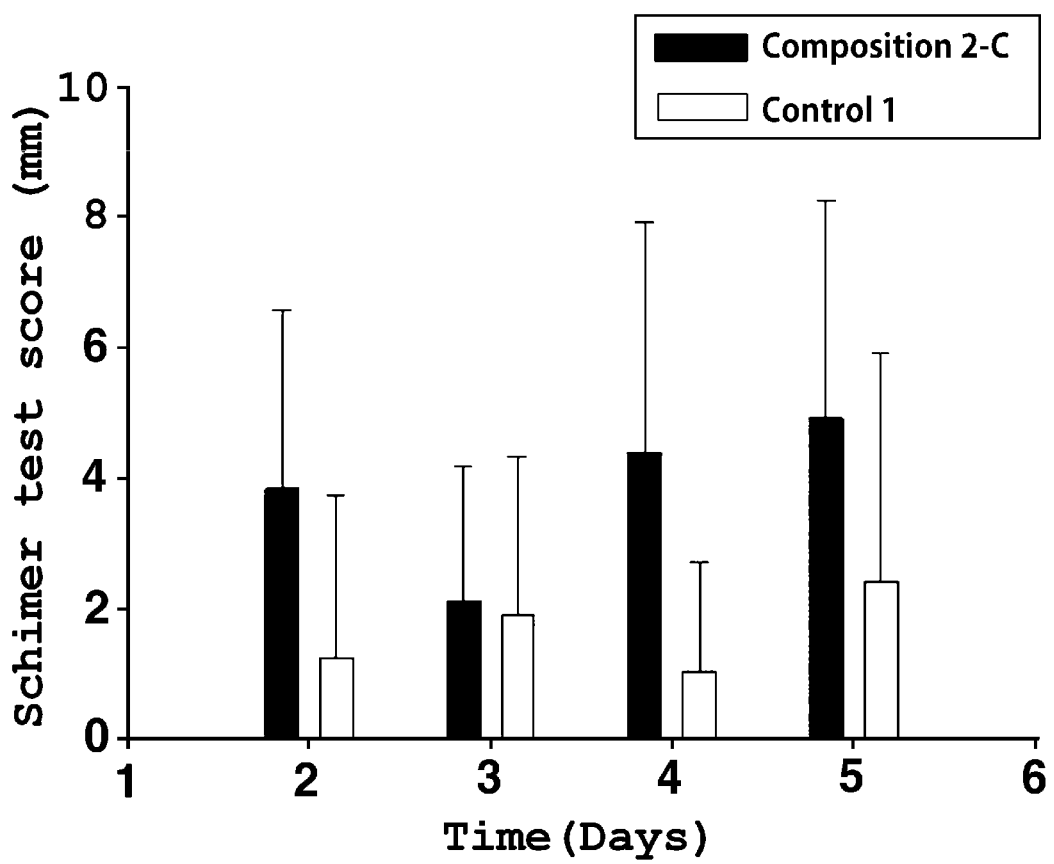
FIG. 4 is a result of a drug efficacy test through Schirmer's tear test performed for an ophthalmic composition according to an exemplary embodiment of the present invention and control eye drops (control 1).

The efficacies of the ophthalmic compositions of the present invention were evaluated by difference in amount of tears between the right eye (the dry eye syndrome-induced group) and the left eye (the dry eye syndrome-induced group treated with a therapeutic agent, the composition 2-C or Restasis®) of an individual, and the results are shown in FIG. 4.

As shown in FIG. 4, it can be seen that, compared to the Control 1-treated group, the composition 2-C-treated group had amounts of tears increasing 3.1, 1.1, 4.3, and 2.0 times after 2, 3, 4 and 5 days of the test, respectively.

The results mean that the ophthalmic composition of the present invention had an excellent therapeutic effect on the dry eye syndrome.

While the invention has been shown and described with reference to certain exemplary embodiments thereof, it will be understood by those skilled in the art that various changes in form and details may be made therein without departing from the spirit and scope of the invention as defined by the appended claims.

INDUSTRIAL APPLICABILITY

According to the present invention, a cyclosporine-containing nanoemulsion ophthalmic composition does not cause irritation to eyes such as blurred vision when eye drops are applied, enables storage for a long time due to increased physiochemical stability, and is stable since it does not use a high pressure homogenizer, so that it can be useful as cyclosporine-containing eye drops.

The invention claimed is:

1. A nanoemulsion ophthalmic composition, comprising: 0.01 to 1 wt % of cyclosporine; 0.5 to 9.79 wt % of polyethoxylated castor oil or polyethoxylated hydrogenated castor oil; and 90 to 99.29 wt % of phosphate buffer, wherein the composition does not contain any other type of oil or emulsifier.

2. The composition according to claim 1, wherein the nanoemulsion has an average particle size of 100 nm or less.

3. The composition according to claim 2, wherein the nanoemulsion has an average particle size of 50 nm or less.

4. The composition according to claim 1, wherein the cyclosporine is cyclosporine A.

5. The composition according to claim 1, further comprising a thickening agent.

6. The composition according to claim 5, wherein the thickening agent is at least one selected from the group consisting of hyaluronic acid or a salt thereof, chitosan, hydroxypropylmethylcellulose, hydroxypropylcellulose, hydroxyethylcellulose, polyvinyl pyrrolidone, carboxymethylcellulose, a carbomer, glycerin, and polyethyleneoxide.

7. The composition according to claim 6, wherein the thickening agent is hyaluronic acid or a salt thereof.

8. The composition according to claim 5, wherein the thickening agent is included at 0.1 to 5 wt % of the entire ophthalmic composition.

9. The composition according to claim 1, further comprising ethanol.

10. The composition according to claim 9, wherein the ethanol is included at 0.1 to 3 wt % of the entire ophthalmic composition.

* * * * *